(12) United States Patent
Thom et al.

(10) Patent No.: US 10,987,629 B2
(45) Date of Patent: Apr. 27, 2021

(54) METHOD FOR REMOVING BIOPOLYMER AGGREGATES AND VIRUSES FROM A FLUID

(75) Inventors: Volkmar Thom, Goettingen (DE); Bjoern Hansmann, Goettingen (DE)

(73) Assignee: Sartorius Stedim Biotech GmbH, Goettingen (DE)

(*) Notice: Subject to any disclaimer, the term of this patent is extended or adjusted under 35 U.S.C. 154(b) by 0 days.

(21) Appl. No.: 14/125,755

(22) PCT Filed: Apr. 28, 2012

(86) PCT No.: PCT/EP2012/001840
§ 371 (c)(1),
(2), (4) Date: Dec. 12, 2013

(87) PCT Pub. No.: WO2012/175156
PCT Pub. Date: Dec. 27, 2012

(65) Prior Publication Data
US 2014/0116941 A1    May 1, 2014

(30) Foreign Application Priority Data

Jun. 24, 2011    (DE) ........... 10 2011 105 525.1

(51) Int. Cl.
*B01D 61/16*    (2006.01)
*A61L 2/00*    (2006.01)
*B01D 61/14*    (2006.01)

(52) U.S. Cl.
CPC ............ *B01D 61/16* (2013.01); *A61L 2/0017* (2013.01); *B01D 61/145* (2013.01);
(Continued)

(58) Field of Classification Search
CPC .......... B01D 2311/04; B01D 2311/165; B01D 2311/2649; B01D 2311/2626;
(Continued)

(56) References Cited

U.S. PATENT DOCUMENTS 5,093,197 A    3/1992 Howard et al.
5,521,154 A *  5/1996 Garlick ................ C07K 14/805
                                            514/13.4
(Continued)

FOREIGN PATENT DOCUMENTS

DE    101 14 537       10/2002
DE    10114537 A1      10/2002
(Continued)

OTHER PUBLICATIONS

Subramanian Senthilkannan Muthu, Assessing the Environmental Impact of Textiles and the Clothing Supply Chain 15 (2014).*
(Continued)

*Primary Examiner* — Krishnan S Menon
*Assistant Examiner* — Brad Gordon
(74) *Attorney, Agent, or Firm* — Gerald E. Hespos; Michael J. Porco; Matthew T. Hespos (57) ABSTRACT

The present invention relates to a method for removing biopolymer aggregates and viruses from a fluid. In a first step, the biopolymer aggregates are selectively removed by filtration through a porous, polyamide-comprising shaped body having a native surface. In a second step, the biopolymer aggregate-free fluid is filtered through at least one suitable virus-retentive membrane.

1 Claim, 4 Drawing Sheets

(52) U.S. Cl.
CPC ........ *B01D 61/147* (2013.01); *A61L 2202/22* (2013.01); *B01D 2311/04* (2013.01); *B01D 2311/2626* (2013.01); *B01D 2311/2688* (2013.01)

(58) Field of Classification Search
CPC .......... B01D 2311/2688; B01D 61/145; B01D 61/16; B01D 61/142; B01D 61/147; B01D 15/00; B01D 15/08; B01D 39/06; B01D 2313/02; B01D 2313/125; B01D 2313/243; B01D 2313/44; B01D 2321/04; B01D 2325/36; B01D 63/025; Y10T 436/255; Y10T 436/25375; B01J 20/10; B01J 20/28007; B01J 20/28023; B01J 20/28028; B01J 20/28057; B01J 20/28016; B01J 20/28033; B01J 2220/42; B82Y 30/00; C02F 2303/04
USPC ............ 210/638, 651, 505, 635, 645, 198.1, 210/500.1, 502.1, 503, 510.1, 641, 650, 210/656, 660, 661, 669, 767, 806
See application file for complete search history.

(56) References Cited

U.S. PATENT DOCUMENTS

| | | | |
|---|---|---|---|
| 5,531,899 | A | 7/1996 | Yen et al. |
| 7,118,675 | B2 | 10/2006 | Siwak et al. |
| 7,465,397 | B2 * | 12/2008 | Siwak et al. ................. 210/645 |
| 7,517,537 | B1 * | 4/2009 | Gottlund ...................... 424/443 |
| 2003/0036088 | A1 | 2/2003 | Bogedain et al. |
| 2003/0146156 | A1 * | 8/2003 | Siwak ................. B01D 61/142 210/651 |
| 2009/0326211 | A1 | 12/2009 | Boyette et al. |

FOREIGN PATENT DOCUMENTS

| | | |
|---|---|---|
| EP | 1 624 950 | 7/2007 |
| JP | 2001162146 A | 6/2001 |
| JP | 2001-513644 | 9/2001 |
| JP | 2005145852 A | 6/2005 |
| JP | 2006-151840 | 6/2006 |
| JP | 2006151840 A * | 6/2006 |
| JP | 2008094722 A | 4/2008 |
| JP | 2010047527 A | 3/2010 |
| WO | 03/066669 | 8/2003 |
| WO | 2004/103530 | 12/2004 |
| WO | 2010/098867 | 9/2010 |
| WO | 2011031397 A1 | 3/2011 |

OTHER PUBLICATIONS

David M. Teegarden, Polymer Chemistry: Introduction to an Indispensable Science 22 (2004).*
Mark Alger, Polymer Science Dictionary 492 (1997).*
Rachel Houp, Ultrafiltration and Diafiltration, 15 J. Validation Tech., 1, 1 (2009).*
Fox et al., Dairy Chemistry and Biochemistry 333 (2d. ed., 2015).*
Brown et al., Increasing Parvovirus Filter Throughput of Monoclonal Antibodies Using Ion Exchange Membrane Adsorptive Pre-filtration, 106 Biotechnol. Bioeng 627, 627-637 (2010).*
Fox et al., Dairy Chemistry and Biochemistry 333 (2d. ed., 2015). (Year: 2015).*
Pall Corporation, Endotoxin Removal, p. 1 (2007). (Year: 2010).*
He Li and George Lykotrafitis, Erthrocyte Membrane Model with Explicit Description of the Lipid Bilayer and the Spectrin Network, 107 Biophys J, 642, 642-653 (2014). (Year: 2014).*
Pall Corporation, Endotoxin Removal, p. 1 (2007). (Year: 2010).*
Brown et al., Increasing Parvovirus Filter Throughput of Monoclonal Antibodies Using Ion Exchange Membrane Adsorptive Pre-filtration, 106 Biotechnol. Bioeng 627, 627-637 (2010). (Year: 2010).*
Sandals et al., Prevalence of bovine parvovirus infection in Ontario dairy cattle, 59 Can. J. Vet. Res. 81, 81-86 (1995) (Year: 1995).*
A. Omar & C. Kempf, Removal of neutralized model parvoviruses and enteroviruses in human IgG solutions by nanofiltration, 42 Transfusion 1005, 1005-1010 (2002). (Year: 2002).*
Saxena et al.—"Membrane-based techniques for the separation and purification of proteins: An overview"—Advances in Colloid and Interface Science, Elsevier, NL—vol. 145, No. 1-2, Jan. 30, 2009—pp. 1-22.
A. Brown et al.—"Increasing Parvovirus Filter Throughput of Monoclonal Antibodies Using Ion Exchange Membrane Adsorptive Pre-filtration", Bioseparations and Downstream Processing, Biotechnology and Bioengineering, DIO 10.1002/bit.22729, 2010 Wiley Periodicals, Inc.—pp. 1-32.
International Search Report dated Jun. 5, 2012.
Translation International Preliminary Report on Patentability.
Non-patent Publication entitled "Investigations of Prion and Virus Safety of a New Liquid IVIG Product"—Biologicals, 2008, vol. 36, p. 239-247.
Translation of Japanese Office Action dated Mar. 28, 2016.
European Office Action dated Jan. 26, 2018.
"Kumano Kotaro, Japanese Journal of Clinical Immunology, Japan 2008, vol. 31, No. 6, p. 448-453".
Japanese Office Action dated Jan. 30, 2018.
Japanese Office Action dated Mar. 26, 2019.
Japanese Final Rejection dated Nov. 27, 2019.

* cited by examiner

METHOD FOR REMOVING BIOPOLYMER AGGREGATES AND VIRUSES FROM A FLUID

BACKGROUND

1. Field of the Invention

The present invention relates to a method for removing biopolymer aggregates and viruses from a fluid.

2. Description of the Related Art

Biopolymer aggregates, for example aggregates of proteins, and viruses are frequently undesired contaminants in fluids obtained by biotechnological methods, such as protein and peptide solutions. Public health authorities prescribe the removal of said contaminants from the fluid before it is used therapeutically.

Protein solutions, for example immunoglobulins in blood plasma, or solutions comprising recombinant proteins or natural proteins generally contain a detectable proportion of dimers and higher aggregates of said proteins. Prior to parenteral administration to patients, depletion of the aggregates is necessary. In general, an aggregate content of in total less than 1%, based on the total protein content of the solution, is striven for. The removal of said aggregates by means of size-exclusion filtration is not advantageous from a technical point of view, since the filters used become blocked during said filtration. As an alternative, methods which can remove impurities, for example aggregates of biopolymers, by means of selective affinity binding to chromatographic columns, such as ion exchangers, have been established.

For the depletion of viruses as contaminants from protein solutions which are used therapeutically, size-exclusion filtration is known to be an effective process which can be used reliably on all virus species and under a large range of conditions. The filtration of protein solutions in order to deplete small, nonenveloped viruses is a robust step recognized by public health authorities for reducing virus concentration in protein solutions originating from biological sources. In said filtration, it is necessary to have in one production process at least two robust virus-depletion methods which act differently.

The requirements typical for filtration procedures are applicable to the effective elimination of viruses from protein solutions: Separation selectivity should lead to a reduction in the titer, i.e. the virus concentration, by a factor of at least 103. The water permeability of the filtration membrane used for the removal of the viruses should be maximal. By contrast, the tendency toward blockage, i.e. the reduction in flow capacity owing to an obstruction by accompanying components, or the closure of filtration membrane pores, should be minimized. Owing to the simultaneously necessary passage of the therapeutic proteins as target compounds, the hydrodynamic radius of which is of a similar order of magnitude to that of the viruses to be retained, the production of suitable so-called parvovirus filters is complicated compared to microfiltration membranes for other applications. The small difference in size between proteins and viruses results in the parvovirus filters being especially sensitive with respect to blockage and, compared to microfilters, in a high demand on the purity of the solution to be filtered.

Because of these high demands on product purity, the parvoviral filtration is carried out relatively late in the process sequence for producing recombinant proteins or blood plasma products. Typically, the filtration is preceded by chromatographic separation and purification processes. Highly relevant to the viral filtration is the requirement that no extractable constituents (leachables) or particles are released into the filtrate from the filtration media used. The release of such contaminants occurs with preference when kieselguhr-containing depth filters are used.

U.S. Pat. No. 7,118,675 B2 discloses a method for selectively removing protein aggregates and viruses from a protein solution, wherein, in a first step, the protein solution is filtered through one or more layers of a charged or surface-modified microporous membrane in order to retain the aggregates. In a second step, the protein aggregate-free filtrate is filtered through one or more ultrafiltration membranes, whereby the virus content is reduced by at least three powers of ten. This method, which has proved effective in principle, requires, as a function of the protein solution to be processed and the aggregates to be removed, individual adjustment of the pH and the conductivity of the protein solution. These aforementioned parameters influence, on their part, the optimal selection of a suitable charged or surface-modified membrane for the first step of the method. As an alternative, in the first step, one or more layers of a depth filter can be used in addition to the microporous membranes.

This optimization problem has already been identified by A. Brown et al. in "Increasing Parvovirus Filter Throughput of Monoclonal Antibodies Using Ion Exchange Membrane Adsorptive Pre-Filtration", Bioseparations and Downstream Processing, Biotechnology and Bioengineering, DOI 10.1002/bit.22729, 2010 Wiley Periodicals, Inc. For the removal of biopolymer aggregates from virus-containing solutions, charged membranes can be used effectively only within a narrow pH range and at low salt concentrations because undesired competition between the binding of salt ions and the antibodies as target proteins occurs in said membranes at high salt concentrations.

A. Brown et al. describe the use of charged membrane prefilters to increase the filtration capacity of downstream Viresolve® parvovirus filters. Here, the prefilters remove aggregates of monoclonal antibodies, the monomers of the antibody being the target product. For cation-exchanging membranes having sulfonic acid ligands (Mustang® S) as virus prefilter, the filtration capacities of a parvovirus filter were determined within a pH range of between 4 and 7 and at conductivities between 3 mS/cm and 25 mS/cm. The filtration capacities achieved, defined as V50 (filtration volume in the case of a permeability drop of 50% with respect to the start of filtration), show a strong dependence on pH and conductivity, which is additionally influenced by the monoclonal antibody used. The pH dependence is explained by the change in the net charge of the proteins and the aggregates. The dependence on conductivity is attributed to shielding of the charged groups of the prefilter by salts. In the case of the monoclonal antibody used from Chinese hamster ovary cells, an optimum (sweet spot) arises within a pH range of 5 to 6 and at a conductivity between 5 mS/cm and 12 mS/cm. The differences between the abovementioned optimized conditions of the sweet spot and other suboptimal ranges of pH and conductivity differ from one another by up to a factor of 9 with regard to V50.

When using charged membranes for aggregate removal, these optimized conditions for the "sweet spot" have to be ascertained on a individual basis for each protein, this optimization amounting to great effort for successful application of this method.

EP 1 624 950 B1 discloses a method for selectively removing protein aggregates and viruses from a protein solution, wherein, in a first step, the aggregates are retained by a fibrous pad and plugging constituent removing media, whereas, in the subsequent second step, the viruses are retained by at least one ultrafiltration membrane, whereby the virus content is reduced by at least three powers of ten. The fibrous pad can contain one or more layers of microporous membranes composed, for example, of polyamide, regenerated cellulose, poly(ether)sulfone, polyimide or PVDF, which, on their part, are filled with charged particles, known from U.S. Pat. No. 5,531,899 or 5,093,197, for improved aggregate retention. As charged particles, use is made of, for example, particles based on Diphonix cation-exchange resins or particles having surface silanol groups in polyolefin membranes. As an alternative, the membrane to be used as prefilter can be filled with silica gel particles.

The use of membranes filled with charged particles results here in the aforementioned optimization problem with regard to pH and conductivity of the protein solution to be processed.

With regard to undesired release of particles into the filtrate containing the target proteins, the use of plugging constituent removing media in the first step of the method can be problematic.

A further method in which a charged membrane is likewise used as prefilter for the downstream virus filter is disclosed by U.S. Pat. No. 7,465,397 B2. Viruses and protein aggregates are removed from a protein solution in at least two steps in this method, in which surface- or charge-modified polyamide membranes are used in the first filtration stage, whereas the downstream ultrafiltration module for virus removal comprises polyamide membranes which are not modified on their surface.

US 2009/0326211 A1 discloses a method for selectively removing large microbiological particles, such as algae, fungi, amoebas, or inorganic particles from a water sample containing microorganisms, such as *Legionella pneumophila* or viruses. Unlike the other documents already mentioned, removal is effected here according to the principle of size-exclusion filtration and can be carried out in a similar manner largely independent of the material of the filter. However, removal according to the principle of size-exclusion filtration likewise does not solve the optimization problem already discussed for the other documents with regard to pH and conductivity of the protein solution to be processed.

In the first step of the method according to US 2009/0326211 A1, the particles are retained by a prefilter consisting of a steel screen, glass fibers, polypropene, polyethersulfone, nylon, PVC, PTFE, polyester, polycarbonate or polyester, whereas the microorganisms pass through the prefilter. The filtrate containing the microorganisms is subsequently fed to a main filter having a smaller pore size, by means of which the microorganisms are retained. Subsequently, the microorganisms can be subjected to lysis on the main filter for analysis. The material of the main filter is selected from the group of the materials which are also used for the prefilter.

It is an object of the present invention to provide a method which overcomes the aforementioned disadvantages of the prior art and which permits the selective removal of biopolymer aggregates and viruses from biotechnological fluids in a simple and cost-effective manner. Said method shall avoid the use of complicated-to-produce charged or surface-modified membranes as virus prefilters and of materials which can release particles into the filtrate. Furthermore, the method to be provided shall allow the reliable selective removal of said aggregates and viruses across a wide range for the pH and conductivity of the protein solution to be processed.

SUMMARY OF THE INVENTION

The present invention provides a method for removing biopolymer aggregates and viruses from a fluid, comprising the following steps:

(a) filtering the fluid containing the biopolymer aggregates and viruses through a porous, polyamide-comprising shaped body, the internal and external surfaces of which have the same chemical and physical properties as the shaped-body matrix which is enclosed by the surfaces, wherein the biopolymer aggregates are selectively depleted from the fluid by adsorption, whereas the viruses permeate through the shaped body; and (b) filtering the fluid from step (a) through at least one membrane having a molecular weight cut-off of from 100 to 1000 kD, wherein the content of viruses in the fluid is reduced by at least 99.9% with respect to the content of viruses prior to carrying out step (a).

According to the invention, the term "biopolymer aggregates" is not subject to any particular restriction. In a preferred embodiment of the present invention, the biopolymer aggregates are selected from the group of the dimers, trimers and multimers of peptides, proteins, nucleic acids or mixtures thereof.

According to the invention, the term "virus" is not subject to any restriction, i.e. the term encompasses both enveloped (e.g. MLV) and small, nonenveloped viruses (parvoviruses) such as, for example, PPV or MVM.

According to the invention, the term "fluid" is not subject to any restriction. In a preferred embodiment of the present invention, the fluid comprises a blood plasma product, a protein solution obtained from a cell culture, a protein solution obtained from extraction of animal or plant products, or a protein solution obtained from microorganisms.

In step (a) of the method according to the invention, the biopolymer aggregates are selectively removed by filtration through a porous, polyamide-comprising shaped body, whereas the viruses and target compounds permeate through the shaped body. According to the invention, "selective removal of biopolymer aggregates" is understood to mean that the biopolymer aggregate content of the fluid is reduced after the filtration with respect to the starting biopolymer aggregate content. This selective removal of the biopolymer aggregates in the first step of the method according to the invention can thus advantageously prevent blockage of the pores of virus-retentive membranes in step (b) of the method. According to the invention, the filter material in step (a) is a native surface of a polyamide in porous form. In this connection, native means that the internal and external surfaces of the polyamide-comprising shaped body have the same chemical and physical properties as the matrix (the base material).

According to the invention, polyamide is understood to mean a polymer composed of repeating units which are covalently bonded to one another by means of amide functions. The monomer units can be aliphatic and/or aromatic and be joined to one another via ring opening or polycondensation. In a preferred embodiment of the present invention, the porous, polyamide-comprising shaped body comprises an aliphatic and/or aromatic polyamide having no more than five different repeat units (monomers). Among the aforementioned monomers, particular preference is given to ε-caprolactam, 1,6-hexanedioic acid and 1,6-hexanediamine or sebacic acid. In a particularly preferred embodiment, the porous, polyamide-comprising shaped body consists of an aliphatic and/or aromatic polyamide having no more than five different repeat units. In a further preferred embodiment, a polyamide consisting only of aliphatic monomer units is used. In a particularly preferred embodiment of the method according to the invention, the polyamide used is nylon-6 and/or nylon-6,6.

According to the invention, the porous, polyamide-comprising shaped body itself is not subject to any restriction in terms of its form; for example, it can be present in the form of fibers, for example as nonwoven, as woven fabric, as porous membrane, as monolith, as gel, as bed of particles, or the like. According to the invention, the pore size of the porous, polyamide-comprising shaped body is not subject to any restriction. In a preferred embodiment of the present invention, the polyamide surface has a pore size smaller than 0.5 μm. In a further preferred embodiment of the present invention, the polyamide-comprising shaped body comprises a microporous membrane, a monolith, a gel, or a bed of particles. In a particularly preferred embodiment, the polyamide-comprising shaped body is a microporous membrane.

In step (b) of the method according to the invention, the fluid from step (a) is filtered through at least one virus-retentive membrane. In this connection, the membrane filter is considered to be virus-retentive if the membrane filter achieves at least 99.9% depletion of small viruses, for example PPV (plum pox virus, sharka virus), and model systems, such as the bacteriophage PP7. In a preferred embodiment of the present invention, at least 99.99% depletion of enveloped viruses is additionally achieved. In this connection, a person skilled in the art will easily select a suitable virus-retentive membrane which is known from the prior art and which meets this standard and, in addition, allows the target molecules to permeate.

According to the invention, the membrane has a molecular weight cut-off of from 100 to 1000 kD. In this connection, the molecular weight cut-off (MWCO) of a membrane refers to the nominal molecular weight of molecules and particles of which 90% can pass through the membrane. To this end, a person skilled in the art will, in a manner known to him or her, compare the molecular weight distribution of a filtrate of the membrane to be investigated of a mixture of dextrans of varying molar mass with the unfiltrate in a gel permeation chromatography procedure, with the flow through the membrane being adjusted to 0.0001 cm/s.

In a preferred embodiment of the present invention, the membrane used in step (b) comprises polyethersulfone, polysulfone, polypropylene, polytetrafluoroethene, polyamide, polyimide, polyvinylidene fluoride, cellulose, cellulose derivatives or mixtures thereof. In a particularly preferred embodiment of the present invention, the membrane consists of polyethersulfone, polysulfone or mixtures thereof.

The method according to the invention can be used effectively across a wide pH range of the fluid. In a preferred embodiment of the present invention, the pH of the fluid during steps (a) and (b) is between 5 and 9.

Owing to the use of a porous, polyamide-comprising membrane, the method according to the invention has particular advantages over the use of known chromatographic columns. By selectively removing the biopolymer aggregates in the first step of the method according to the invention, blockage of the pores of virus-retentive membranes can be advantageously avoided in step (b) of the method. It was found that, surprisingly, in the case of filtration of a fluid through a porous, polyamide-comprising shaped body having a native surface prior to filtration across a virus-retentive membrane, there was a distinct increase in the filtration capacity of the virus-retentive membrane compared to the use of prefilters composed of other materials, for example polyethersulfone, and in particular of membranes having charged surfaces or surfaces chemically or physically modified with respect to the membrane matrix. The increase in the filtration capacity of virus filters works independently of the net charge of the protein aggregates, and the ratio between volume of the protein solution and the surface area influences the filtration capacity proportionally. Furthermore, the surface effects of the polyamide can be combined with a size-exclusion effect. Advantageously, the increase in the filtration capacity is independent of the pH of the fluid in the range of pH=5 to 9, and this distinguishes the method according to the invention from the methods known to a person skilled in the art using charged or surface-modified membranes. Furthermore, the porous surface of the polyamide-comprising shaped body advantageously exhibits only a low release of organic carbon and particles compared to typical depth filter materials which are described for the removal of biopolymer aggregates and are therefore of only limited suitability in typical processes for depleting viruses from protein solutions. In addition, the porous polyamide surfaces used for the method according to the invention, for example in the form of membranes, are distinctly more conveniently available compared to classic chromatography media. Accordingly, separation by means of the method according to the invention using the same volume of medium is, advantageously, not only distinctly more selective and faster than is possible with the methods known to date, but also in addition distinctly more cost-effective.

DETAILED DESCRIPTION OF THE PREFERRED EMBODIMENTS

The present invention will now be more particularly elucidated with reference to the following nonrestricting examples.

EXAMPLES

In the following examples, the filtration capacity Vmax is the asymptotic value for the filtration volume at 100% blockage of the filter, obtained as the reciprocal of the slope of the line from a plot of the quotient t/V against t in the case of filtration at constant pressure as described in Ho et al., Journal of Colloid and Interface Science 232, 389-399 (2000) (equation 1):

$$\frac{t}{V} = \frac{1}{V_{max}} \cdot t + \frac{1}{Q_0}$$ (equation 1)

In the equation, t refers to the filtration time, V the filtration volume, Vmax the filtration capacity and Q0 the initial flow in the case of the filtration at constant pressure.

Example 1: Filtration of a Protein Solution of a Monoclonal Antibody from the Cell Line CHO dg44 ST1-C6

The monoclonal antibody in the protein solution originates from the cell line CHO dg44 ST1-C6 and was made available by means of the following method:

Firstly, a cell culture in which the target protein was produced was set up. Culturing took place under usual conditions known to a person skilled in the art, using a Biostat® CultiBag RM single-use bioreactor (Sartorius Stedim Biotech GmbH) with a culture volume of 25 L and an inoculation cell density of 5×10⁵ cells/mL and the growth medium Pro CHO5 (Lonza BE12-766P).

After attainment of the maximum cell density after 9 days, the cells were harvested and purification carried out. In a typical method, the cell suspension was firstly filtered across depth filter layers and particle filters having a pore size of 0.2 µm. The antibody was isolated from the cell-free solution in chromatographic methods, such as protein A affinity chromatography and ion-exchange chromatography.

To prepare the protein solution for the filtration, the purified solution after the chromatographic steps was subjected to ultrafiltration/diafiltration. To this end, a Sartocon Slice, Hydrosart® 30 kD MWCO (3051445901E-SW) filtration cassette having a filtration area of 0.1 m² and a molecular weight cut-off of 30 kD was used. After this step to alter the buffer composition and protein concentration, the solution of the antibody having a concentration of 10 g/L in phosphate buffer, pH 6.6 (Sigma Aldrich, catalog No. P8165), and 10 mM EDTA (Sigma Aldrich, catalog No.: E6758) was obtained.

The protein solution of the monoclonal antibody was guided, in step (a), across a porous polyamide surface composed of nylon-6 in the form of a microporous membrane (pore size 0.2 µm, external area 17.5 cm2). Subsequently, the filtrate from step (a) was filtered, in step (b), across one layer of a virus-retentive membrane, Virosart® CPV Minisart (polyethersulfone membrane, pore size 0.02 µm, area 5 cm², Sartorius Stedim Biotech GmbH), at 1 bar.

Figure 1:
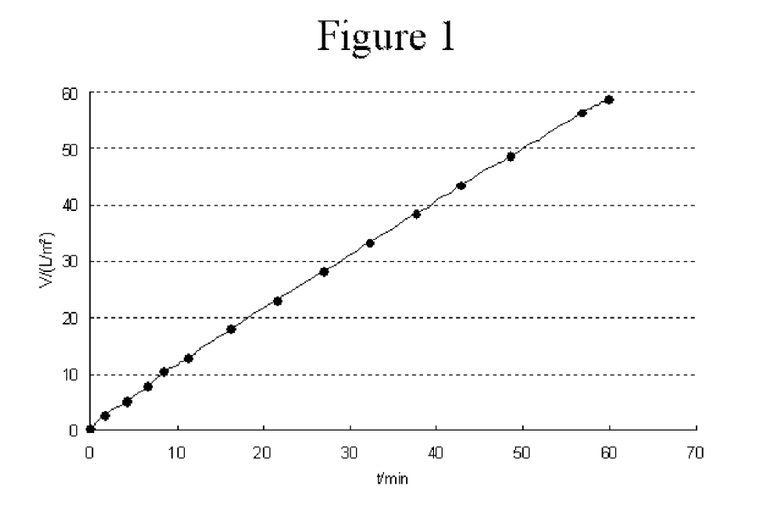
FIG. 1 is a graph that shows the course of filtration of Example 1.
Figure 2:
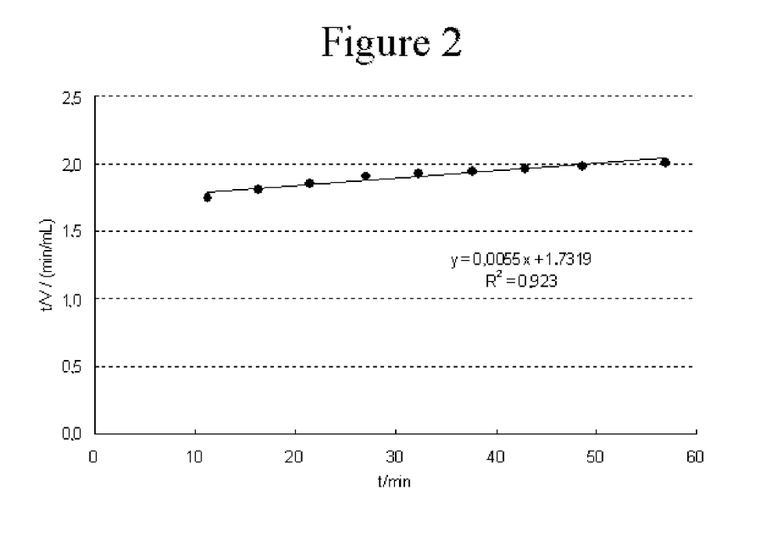
FIG. 2 shows a plot of t/V against t of the filtration shown in FIG. 1.

FIG. 1 shows a graph of the course of the filtration of the monoclonal antibody, where the filtered volume, normalized to an area of 1 m2, is plotted on the y-axis and the filtration time in minutes is plotted on the x-axis. FIG. 2 shows a plot of t/V against t of the same filtration, from which the reciprocal of the slope of the line allows a filtration capacity $V_{max}$ of 365 L/m² to be determined according to equation 1.

Comparative Example 1: Filtration of a Protein Solution of a Monoclonal Antibody from the Cell Line CHO dg44 ST1-C6

The filtration of comparative example 1 was carried out analogously to example 1, with the microporous polyamide membrane having a pore size of 0.2 µm in step (a) having been replaced by a polyethersulfone membrane, Sartopore® 2 (pore size 0.1 µm, area 17.5 cm2, Sartorius Stedim Biotech GmbH). In step (b), the filtrate from step (a) was filtered normally, i.e. in dead-end filtration across one layer of a virus-retentive membrane, Virosart® CPV Minisart (area 5 cm², Sartorius Stedim Biotech GmbH), at 1 bar.

Figure 3:
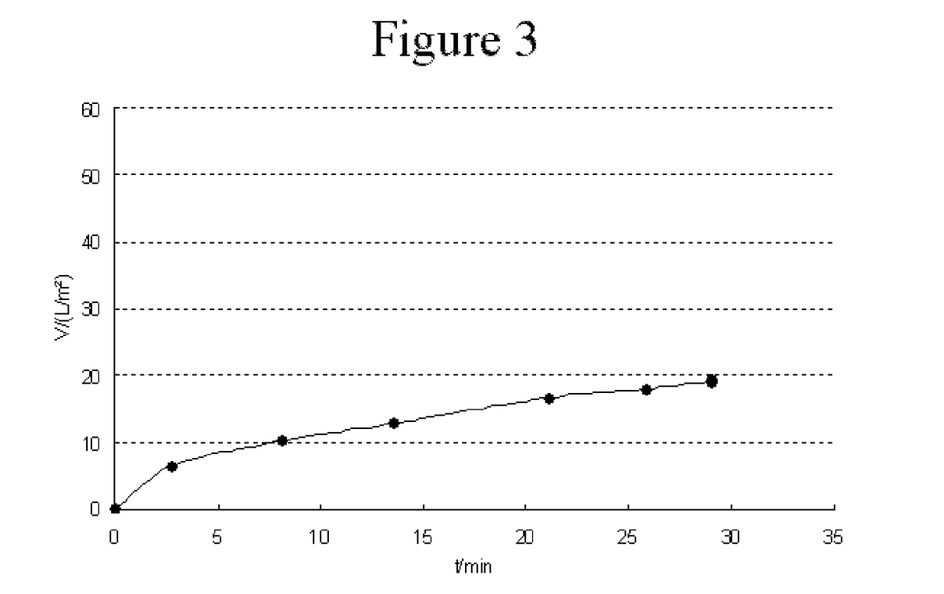
FIG. 3 is a graph that shows the course of filtration of the Comparative Example 1.
Figure 4:
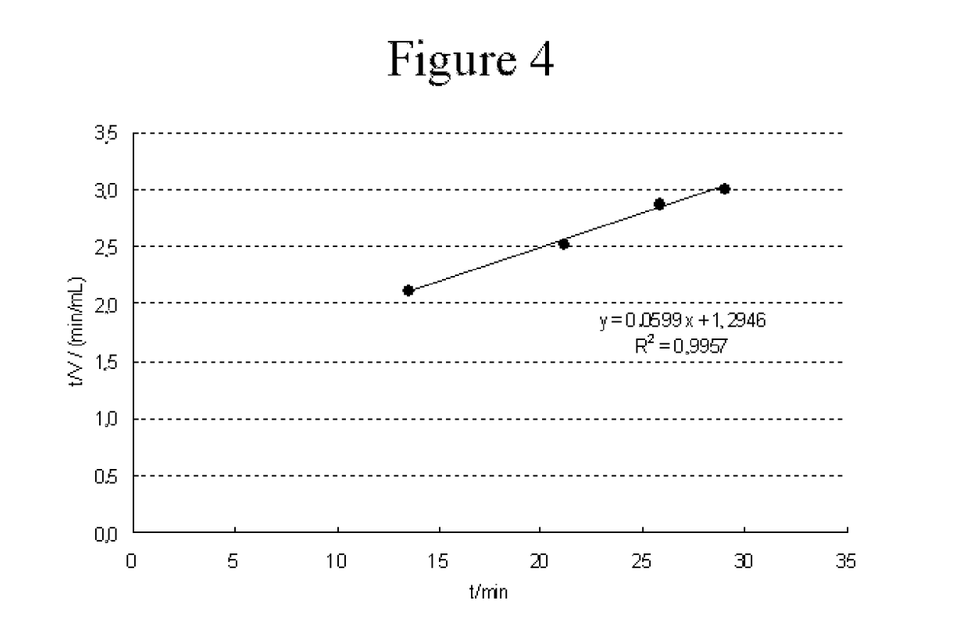
FIG. 4 shows a plot of t/V against t for the Comparative Example 1.

FIG. 3 shows the course of the filtration, with the filtered volume on the y-axis, normalized to an area of 1 m2, and the filtration time in minutes on the x-axis. FIG. 4 shows a plot of t/V against t of the same filtration, from which the reciprocal of the slope of the line allows a filtration capacity Vmax of 33 L/m2 to be determined according to equation 1. The filtration capacity is thus less than 10% of the filtration capacity when using the porous polyamide surface in step (a) of example 1.

Example 2: Filtration of a Solution of a Human IgG Protein

For the filtration, a solution of a human IgG protein (5% strength solution, SeraCare, catalog No. HS-475-1L) diluted with phosphate buffer, pH 6.6 (Sigma Aldrich, catalog No. P8165), and EDTA (Sigma Aldrich, catalog No. E6758) to a concentration of 10 g/L protein and 10 mM EDTA was used. The solution was contacted, in step (a), with a porous polyamide surface composed of nylon-6 in the form of a microporous membrane (pore size 0.1 µm, external area 7 cm²) by filtration normal to the external surface. Subsequently, in step (b), the filtrate from step (a) was filtered normally across a double-layer Virosart® CPV Minisart virus filter (area 5 cm², Sartorius Stedim Biotech GmbH) at 2 bar.

Comparative Example 2: Filtration of a Solution of a Human IgG Protein

Comparative example 2 was carried out analogously to example 2, but, in step (a), with the porous polyamide surface from example 2 having been replaced by a polyethersulfone membrane, Sartopore® 2 (pore size 0.1 µm, area 17.5 cm2, Sartorius Stedim Biotech GmbH).

Figure 5:
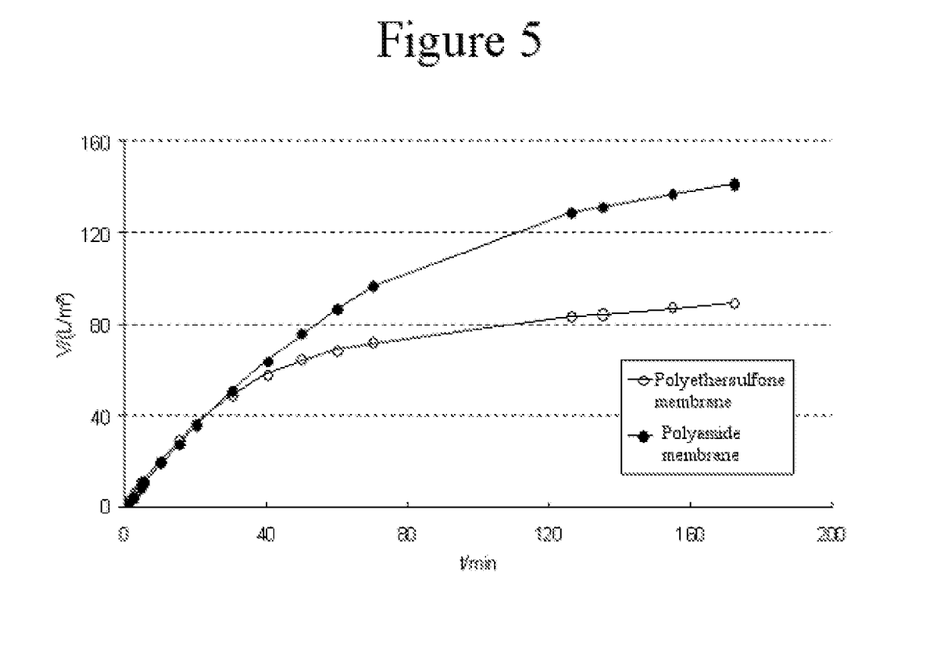
FIG. 5 is a graph that shows the course of filtration of both Example 2 and Comparative Example 2.

FIG. 5 shows a graph of the course of the filtration of the human IgG protein of both example 2 (symbol ●) and comparative example 2 (symbol ○), where the filtered volume, normalized to an area of 1 m2, is plotted on the y-axis and the filtration time in minutes is plotted on the x-axis. The filtration capacity is 109 L/m2 for the filtration with use of the polyethersulfone membrane. The polyamide surface as prefilter results in a filtration capacity of 217 L/m2.

The use of the polyamide surface in the first step increases the filtration capacity in the case of this medium by about a factor of 2 relative to the use of a microporous polyethersulfone membrane.

Example 3: Investigation of pH Dependence

A protein solution was prepared as described in example 1, and the concentration was adjusted to 10 g/L. The pH was adjusted via changes in the buffer composition with the aid of citric acid (Sigma Aldrich, catalog No. C2404) and tris base (2-amino-2-(hydroxymethyl)propane-1,3-diol, Sigma Aldrich, catalog No. T1503) to pH=6.0 and 9.0, respectively. The two protein solutions were adjusted to a uniform conductivity of 15 mS/cm by addition of sodium chloride (Sigma Aldrich, catalog No. S5886). Both solutions were filtered across a Sartopore® 2 polyethersulfone membrane (pore size 0.1 μm) in order to exclude the effects of different pore sizes in further prefiltration steps. In step (a), the protein solutions were filtered across either a charged Sartobind® S membrane (external area 6 cm², Sartorius Stedim Biotech GmbH) or a microporous polyamide membrane (pore size 0.1 μm, external area 6 cm²). In step (b), the solutions were filtered across one layer of a Virosart® CPV parvovirus filter (external area 2.5 cm², Sartorius Stedim Biotech GmbH) and at a differential pressure of 2 bar.

Figure 6:
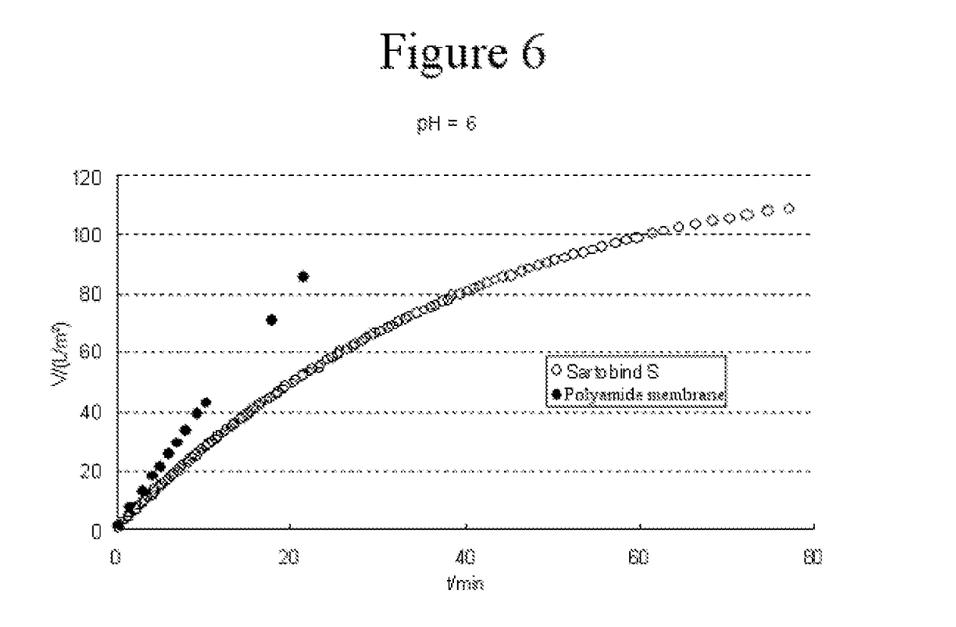
FIG. 6 is a graph that shows the filtration of the protein solution at pH=6 across two different membranes.
Figure 7:
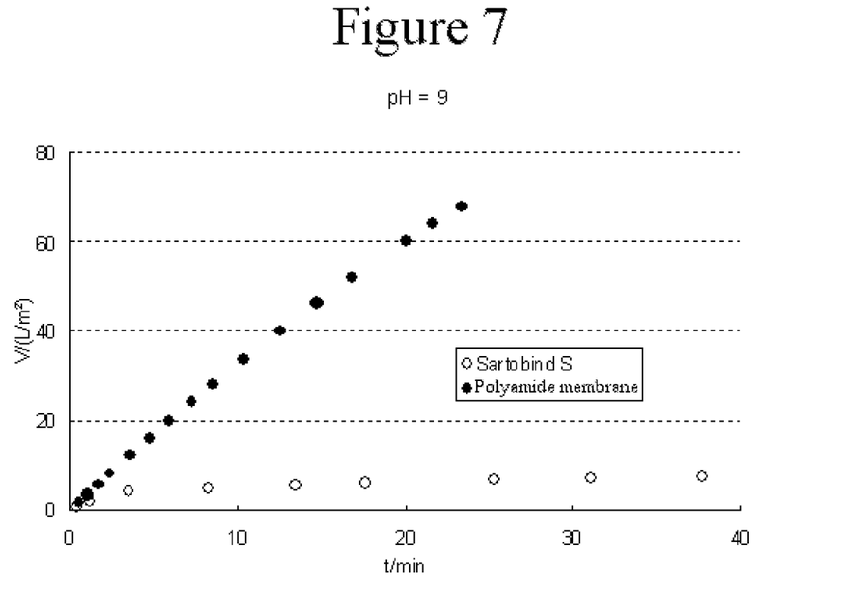
FIG. 7 is a graph similar to FIG. 6, but showing filtration of the protein solution at pH=9.

In FIG. 6, the filtration of the protein solution at pH=6 across the porous polyamide surface in the form of a microporous polyamide membrane (symbol ●) and the filtration of the protein solution at pH=6 across the charged Sartobind® S membrane (symbol ○) are shown together. In FIG. 7, the filtration procedures for the same protein solution at pH=9 are shown. In both figures, the filtered volume, normalized to an area of 1 m2, is plotted on the y-axis and the filtration time in minutes is plotted on the x-axis.

The difference between the Sartobind® S membrane and the polyamide membrane as the first step prior to filtration across a virus-retentive membrane can be clearly seen. The series of filtration experiments implemented here illustrates that the increase in the filtration capacity of a virus-retentive membrane when using polyamide surfaces occurs to a similar extent at different pH levels of the solution, whereas the known process of using charged membranes exhibits a clear pH dependence. At pH=6, the gap, in terms of the filtration capacity of the virus filter, between the polyamide surface ($V_{max}$=550 L/m²) and the charged membrane ($V_{max}$=200 L/m²) is still relatively small. At pH=9, a distinctly larger gap becomes apparent, and in this case the filtration capacity of the virus filter after the charged membrane collapses greatly; with the charged membrane, only $V_{max}$=8 L/m² is achieved. By contrast, in the case of use of the polyamide surface before the virus filter, $V_{max}$=260 L/m² is achieved.

Example 4: Depletion of Biopolymer Aggregates and Viruses

Example 4 shows a repeat of example 1 in a slightly modified form and demonstrates in addition the depletion of the viruses by the method according to the invention.

A protein solution of a monoclonal antibody from the cell line CHO dg44 ST1-C6 was prepared as described in example 1. However, before being used as filtration medium, the protein solution was admixed with a solution of PP7 bacteriophage, a recognized model system for small, nonenveloped viruses, and so the solution contained 10 g/L protein and 4.5·10⁷ pfu/mL (plaque forming units) of the bacteriophage. The filtration was carried out twice analogously to example 1, but at 2.0 bar differential pressure. The prefilter used was, in each case, a polyamide prefilter from example 1. As main filter, two virus filters were selected at random from a batch of 200 Virosart® CPV virus filters (No. 41 (symbol ●) and No. 44 (symbol ○)) and used for the filtration. At both 10 L/m² and 20 L/m², a sample was taken and the titer of the bacteriophages was determined in a plaque assay. The results of the titer determination are shown in table 1.

TABLE 1

| No. of main filter* | Filtrate No. | Filtered volume [L/m²] | Filtration time | Upstream titer [pfu/mL] | Downstream titer [pfu/mL] | Log10 ** |
|---|---|---|---|---|---|---|
| 41 | 1.1 | 10 | 4 min 22 s | $4.5 \cdot 10^7$ | $2.0 \cdot 10^1$ | 6.3 |
| 41 | 1.2 | 20 | 9 min 10 s | $4.5 \cdot 10^7$ | $2.0 \cdot 10^1$ | 6.3 |
| 44 | 2.1 | 10 | 4 min 4 s | $4.5 \cdot 10^7$ | $2.0 \cdot 10^1$ | 6.3 |
| 44 | 2.2 | 20 | 8 min 37 s | $4.5 \cdot 10^7$ | $2.0 \cdot 10^1$ | 6.3 |

*Main filter = Virosart CPV virus filter
** The value of 6.3 entered in the column "Log10" indicates that the bacteriophage titer was reduced by $10^{6.3}$ pfu.

Figure 8:
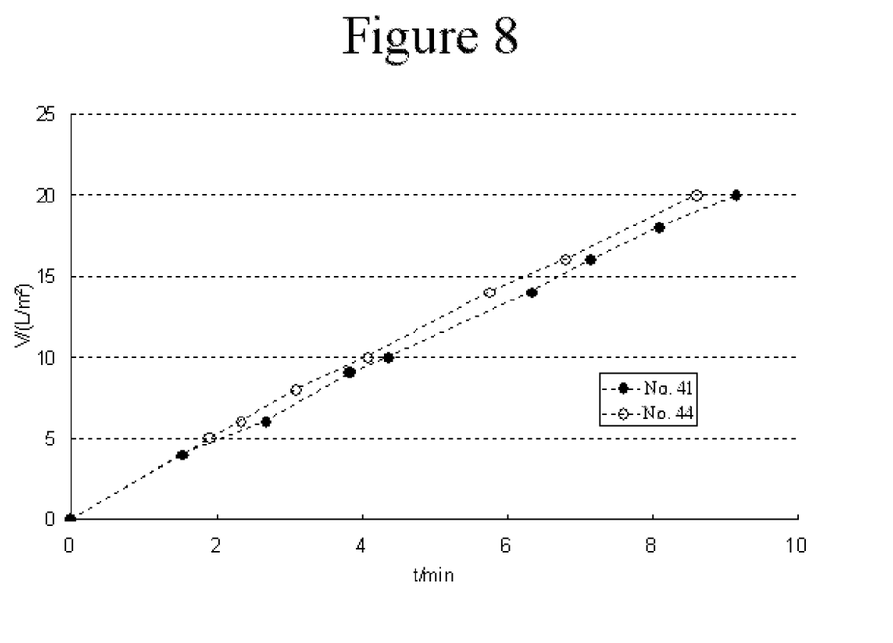
FIG. 8 is a graph that shows the course of filtration for Example 4.

The course of the filtration is shown in FIG. 8. A plot according to equation 1 gives rise to the filtration capacities of 286 L/m2 for main filter No. 41 and 130 L/m2 for main filter No. 44. Because of the low blockage according to the invention at the end point of the filtration, the extrapolation to the maximum capacity is associated with a certain margin of variation.

The invention claimed is:

1. A method for removing biopolymer aggregates and parvoviruses from a fluid, comprising the steps of:
   (a) filtering the fluid containing the biopolymer aggregates and parvoviruses through a porous, polyamide shaped body consisting of nylon-6, the porous, polyamide shaped body having internal and external surface regions and being configured so that all of the internal and external surfaces regions have the same chemical properties, the filtering of the fluid containing the biopolymer aggregates and parvoviruses through the porous, polyamide shaped body causing the biopolymer aggregates to be selectively depleted from the fluid by adsorption, whereas the parvoviruses permeate through the shaped body in a biopolymer aggregate-depleted fluid; and
   (b) filtering the biopolymer aggregate-depleted fluid from step (a) through at least one parvovirus-retentive membrane having a molecular weight cut-off of from 100 to 1000 kD, wherein the content of parvoviruses in the fluid that has passed through the at least one parvovirus-retentive membrane is reduced by at least 99.9% with respect to the content of parvoviruses prior to carrying out step (a); wherein:
   the biopolymer aggregates are selected from the group of the dimers, trimers or multimers of peptides, proteins, nucleic acids or mixtures thereof;
   the fluid comprises a human blood plasma product, a protein solution obtained from a cell culture, a protein solution obtained from extraction of plant products, or a protein solution obtained from microorganisms;
   the pH of the fluid during steps (a) and (b) is 9;
   the porous, polyamide shaped body comprises a microporous membrane; and
   the membrane used in step (b) comprises a material selected from the group consisting of polyethersulfone and polysulfone.

* * * * *